United States Patent [19]

Morita

[11] Patent Number: 4,968,485
[45] Date of Patent: Nov. 6, 1990

[54] ARRANGEMENTS FOR PREPARATIVE ROUTE LEADING TO WATER ANALYSIS

[75] Inventor: Yohzo Morita, Kameoka, Japan

[73] Assignee: Shimadzu Corporation, Kyoto, Japan

[21] Appl. No.: 101,106

[22] Filed: Sep. 25, 1987

[51] Int. Cl.$^5$ .................................................. B01L 3/02
[52] U.S. Cl. ......................................... 422/100; 422/78
[58] Field of Search ...................... 422/79, 50, 100, 62, 422/68

[56] References Cited

U.S. PATENT DOCUMENTS

| | | | |
|---|---|---|---|
| 3,296,435 | 1/1967 | Teal et al. ............................. | 422/79 |
| 3,672,841 | 6/1972 | Freeman et al. ...................... | 422/79 |
| 4,619,902 | 10/1986 | Bernard ................................. | 422/79 |

FOREIGN PATENT DOCUMENTS

| | | | |
|---|---|---|---|
| 0146853 | 9/1983 | Japan ..................................... | 422/79 |
| 0146854 | 9/1983 | Japan ..................................... | 422/79 |
| 60-148766 | 9/1985 | Japan . | |
| 6257163 | 9/1985 | Japan . | |
| 62-80759 | 3/1987 | Japan . | |

*Primary Examiner*—Robert A. Wax
*Assistant Examiner*—T. J. Wallen
*Attorney, Agent, or Firm*—Armstrong, Nikaido, Marmelstein, Kubovick & Murray

[57] ABSTRACT

The disclosure is concerned with arrangements which are disposed on a preparative route leading to water analysis from extraction of water samples. Specifically, an injection unit for injecting water samples into a combustion chamber is improved, wherein a slide block type is employed, but conventional trouble of accumulation of involatile matters around injection site is avoided by change of designs with a slide block and an injection pipe. Next, a micro syringe unit for extraction, measurement of water samples is improved by arranging two syringes connected in branch, wherein a second syringe is intended to feed a quantity of water to dilute a target sample water which will be extracted to a first syringe and in operation, the second dilution water will be influenced to the target first water on route leading to the first syringe. Third, a calibration unit is introduced to mix a reference water sample which has been known of its volume and its concentration into a target water sample to be analyzed. The arrangement includes intervention of a four port two way valve to make communications to both the routes for the sample water and the reference, wherein in operation the reference water is flown to fill one passage in the two way valve while the sample water is flown to fill another passage therein, and then these two passages within the valve are exchanged mechanically to displace the sample water with the reference. Introduction of such calibration will give more correct results of water analyses.

3 Claims, 3 Drawing Sheets

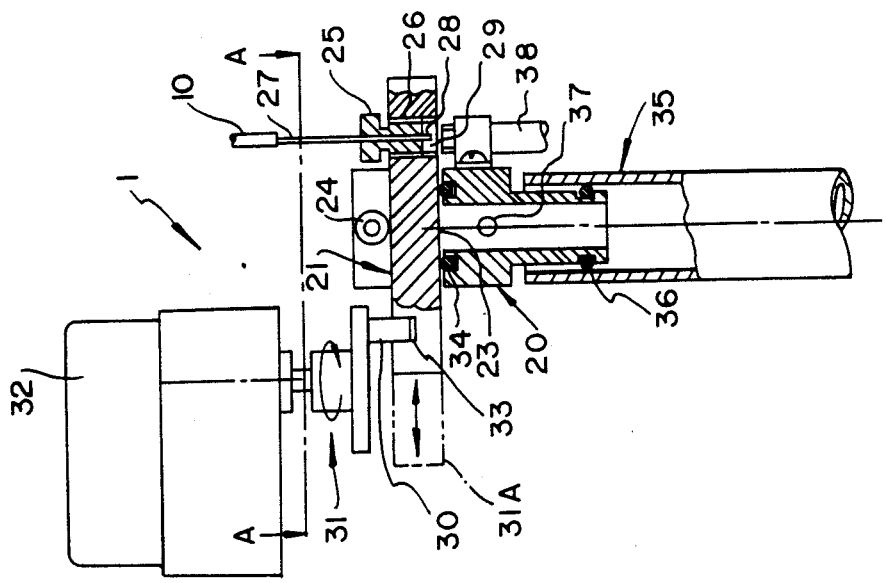

ARRANGEMENTS FOR PREPARATIVE ROUTE LEADING TO WATER ANALYSIS

FIELD OF THE INVENTION

This invention relates to arrangements for preparative route leading to feed water samples to analytical arrangements of combustion type. In particular, this relates to arrangements on route from extraction step of water samples to injection step thereof into a combustion chamber, which are as a whole included in or attached to an analytical system for determining a carbon content in water.

DESCRIPTION OF THE RELATED ART

The analytical system for determining carbon contents in water, or carbon analyzer of water is required to be so versatile, serviceable in analyzing water samples having largely different carbon contents and other pollutants, and the system is also required to avoid trouble of accumulation of involatile residues which will occur on walls adjacent to a combustion chamber, due to its high temperature working.

U.S. Pat. No. 3,296,435 discloses principal procedures for determining carbon contents in water by combustion method, wherein automatic sample injection was not yet employed and possible problems involved in the procedures as noted hereinabove are not recognized there in the disclosures.

U.S. Pat. No. 3,672,841 discloses a flow selector valve arrangement of slide block type for injecting water samples to a combustion chamber in the process of determining the total carbon (TC), the total organic carbon (TOC) and the total inorganic carbon (TIC). As will be described later, however, this selector valve is not capable of avoiding the problems which are recognized in the present invention, in particular, in the problem of the accumulation as noted.

U.S. Pat. No. 4,619,902 discloses a total organic carbon analyzer which uses rotary valves having six ports to switch flows, but the use of multi port rotary valves in such a manner as disclosed is not adequate to receive a water sample having a low carbon content after high carbon content or a sample having a carbon concentration largely different from that of previously flown one.

SUMMARY OF THE INVENTION

This invention comprises, briefly noted, three featuring units as improvement over prior art, which should be included in arrangements for preparative steps on route from extraction of water samples to injection of the water samples into a combustion chamber which is equipped in a carbon analyzer.

Making reference to these features of the present invention respectively, first, a slide type injection device is employed so that a slide block or a carriage block is allowed to slide air-tightly, but improved in that an injection pipe which is built in the carriage block is not extended through downwardly into top of a subjacent combustion chamber or out of bottom level downwardly of the carriage block, though it was extended so much conventionally. In stead, the downward end of the feed pipe is withheld to extend only in a recess formed on downside of the carriage block so that the end will not obstruct to slide movements for one reason. Whereby troublesome accumulation around there caused by involatile matters contained in sample waters is definitely prevented.

Second, in the step of extracting a water sample which is desired to be diluted rather largely with an exact ratio on the way to the injection, one micro-syringe pump for extracting and pumping is connected, via a branch, with another micro-syringe pump which is adapted to extract and to measure pure water for dilution, so that the two extractions will make confluence through drive-connection.

Third is interposition of a special two-way switch valve for exchanging an equal volume each other. This interposition on the way between the pump site noted above and the injection site noted also above is useful to perform calibrations of carbon concentration with use of a standard solution having a known concentration, as reference. A number of methods are known in order to perform the calibration for the same purpose, but a reference water having an extremely low carbon content (for example, water of 0.5 mg/liter carbon content) is difficult to be prepared, and such is often unstable or inconvenient to handle, but it is easy to obtain a reference water having an ordinary carbon content (for example, 20 mg/liter) and to determine its concentration exactly. Then, a water lot which has been known of its concentration by measurement in advance is flown in one of the two ways, passing through the switch valve and is remained filling the one flow hole through the valve and a sample water to be analyzed is also made to fill another flow hole, wherein intra-volume of one or either hole in the valve is assumed to be known by prior measurement. Thus, working of the valve or exchange of two waters each other will introduce a known quantity of carbon in the reference into in the sample water to be analyzed. And combination of two tries with use of a straight or unintroduced sample and an introduced sample will enable to compute a calibration coefficient.

BRIEF DESCRIPTION OF THE DRAWINGS

FIG. 1A shows an elevation view, with partial breaks, of the injection unit of the present invention.

FIG. 1B shows an side view, with also partial breaks, of the same object.

These drawings are presented by way of illustrating the inventive embodiments. Therefore, these should not be interpreted as limiting the invention and in the following, the invention will be explained with reference to the drawings, attached.

DETAILED DESCRIPTIONS OF THE EMBODIMENTS

Figure 1C:
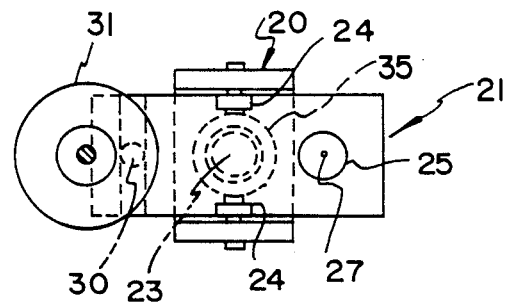
FIG. 1C shows a sectional view cut through a line A—A' with the same object shown in the FIG. 1A.

FIG. 1A, 1B and 1C show an embodiment including the first featuring unit of an injection unit 1. Generally speaking, the injection unit 1 comprises a channel block 20 and a carriage block 21 (or noted as a slide block) with air-tightly fitted each other, wherein the channel block 20 is immobile, and it has a channel section and forms longitudinally a slide space for the carriage block 21, of its upper portion, and of its lower portion, the channel block 20 forms a cylinder extending downward from about a center of the upper portion. And the carriage block 21 is shaped to fit in the channel formed by the channel block 20 and further it is adapted to reciprocally slide on the channel bottom keeping air-tightness with a conjunction opening 23 or top of the cylindrical combustion chamber.

Making more reference, first, to the carriage block 21, it is shaped to be generally a longitudinal square bar, which is horizontally set on the channel bottom and pressed downwardly to keep air-tightness by a pair of rollers 24, projecting inwardly from two opposite side walls of the channel block at a central point thereof. Toward one longitudinal end of the carriage block 21, a reinforcing boss 25 is fitted into a vertical through-bore 26 and, into the boss 25, an injection pipe 27 or a metal-made hollow needle is fitted downwardly and is made to reach the needle end 28 into a recessed space 29 formed downside of the carriage block 21, wherein however the needle end 28 is adjusted or positioned not to extend out of bottom level of the carriage block 21, because such extension will obstruct slide movements of the carriage block. Toward another end of the block 21, an engaging rod 30 coming from a cam mechanism 31 connected with a motor 32 is received in a hole 33 which is formed on the carriage block 21 in order to render reciprocal slide movements. A two opposite arrow mark 31A in a box indicates reciprocal movements.

Turning to the channel block 20, at the conjunction of the upper channel portion with the lower cylinder portion, an elastic O-ring 34 is received in an appropriate annular groove to render smooth slidability, air-tightness and, inside the O-ring 34, formed is the conjunction opening 23, of which diameter is made to be larger than diameter of the round recess 29 formed in the carriage block 21. And the lower portion or cylinder portion is made, towardly of the down end, to fit into the inner surface of the cylindrical combustion chamber 35, with aid of an O-ring 36, in order to make connection with the following analytical devices. And an oxygen supply pipe 37 is connected to the cylinder 35 and a drain pipe 38 for discarding unanalyzed water or washing water samples is equipped externally of the cylinder 35 at such a position that the drain pipe 38 is adapted to receive and let such water flow through itself, after a registering stop of the carriage block 21.

It is to be noted here that location of the drain pipe in FIG. 1A is drawn at right to the cylinder 35, but the same location will be opposite or left to the cylinder in the following drawings, but at which side, right or left, the drain pipe is equipped is a matter of choice and therefore such a change should be interpreted as unessential.

Operations of the injection unit are described as below:

When the analytical system (I) is, as a whole, of which whole arrangements will be generally viewed in later drawings relating to third featuring unit, is set to preliminary actions, for instance, for washing the system and displacing previously existing water samples with a new one to be analyzed, the carriage block 21 is stopped so that the injection pipe 27 is communicated to the drain pipe 38 (see FIG. 1A), whereby some sample water is pumped through a flexible pipe 10 (the numeral 10 will represent all intermediate pipe lines in each drawing) from some water source to pass to the injection needle. Then, site of the needle is switched by a slide move brought by the cam mechanism 31 to the position where the injection needle 27 is registered or communicated to the combustion chamber 35.

The illustrated unit is improved in avoiding accumulation of involatile residues adhering to surfaces around the injection pipe end 28, in a minimum. Another improvement lies in avoidance of after-effect of previous examples, in particular, in the case of presence of large differences in carbon contents between examples in series, because of compact arrangement of the injection site with the combustion. And disassembling work of the injection unit 1, if necessary to clean up after a long-time use, is also eased for its simple attachment structure.

Figure 2:
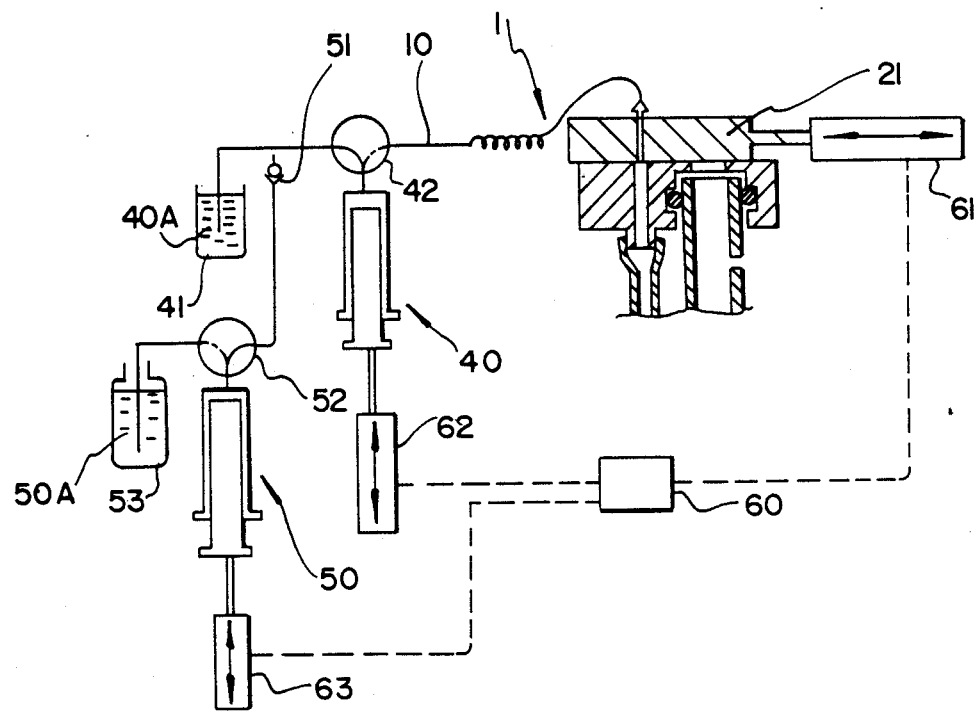
FIG. 2 shows combination of an injection unit, elevationally sectioned, in connection with a micro syringe unit of the present invention.

FIG. 2 shows an embodiment including the second featuring unit, wherein a micro-syringe unit 2 comprises two micro-syringes; one is ordinary, noted as a first, and another or second one is connected in a branch from a pipe between a sample container and the first syringe. This special ladder arrangement is useful to dilute a sample water for the first syringe with simple or second water for the second syringe at an exact high ratio.

As is shown, the first syringe 40 is connected to the sample container 41 and also to an injection unit 1, via a three way valve 42 and on route between the valve 42 and the container 41, the pipe 10 is branched to tie in a check valve 51 which allows only flows tending to the first syringe 40 and, in the following, another three way valve 52, a second syringe 50 and another water container 53 are connected, as shown, so that additional water extraction, measurement and flow thereof are enabled.

Further a control unit 60 is associated, by step motors or other kind of drive means, to the first and second syringes 40, 50 and to the carriage block 21 mounted in the injection unit 1 in order to render displacemental actions to respective devices, and three boxes 61, 62, 63 including respectively two opposite arrows indicate displacemental actions, wherein it is to be noted that the injection unit 1 shown in FIG. 2 is somewhat different from the inventive one described hereinbefore, for the reason of simplifying the drawings.

Then, when a sample water 40A to be extracted into the first syringe 40 is required to be thinned or diluted with a second water 50A, a necessary or calculated volume of the second water 50A for dilution is first transferred into the second syringe 50 by a filling stroke of the plunger of the second syringe, through control action and via the second three way valve 52, in the meanwhile the plunger of the first syringe 40 is stayed at its extension and then the control unit 60 acts to cause simultaneously or almost so a filling stroke of the plunger to the first syringe 40 and an emptying stroke of the plunger to the second syringe 50 so that two flows from the sample container 41 and the second syringe 50 will merge adequately in the first syringe 40. Thereafter, the first three way valve 42 is switched to allow a flow to the injection unit 1 and injection will take place by action of the control unit 60. As is explained above, the dilution process is carried out automatically in the illustrated system.

Figure 3B:
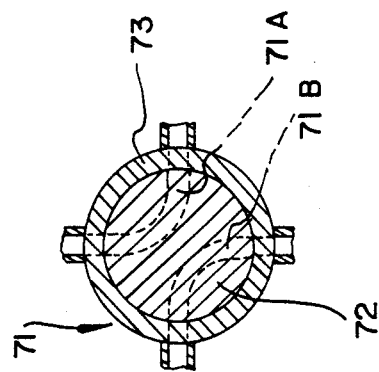
FIG. 3B shows a sectional view of a four-port two-way valve included in the embodiment shown in FIG. 3A.
Figure 3A:
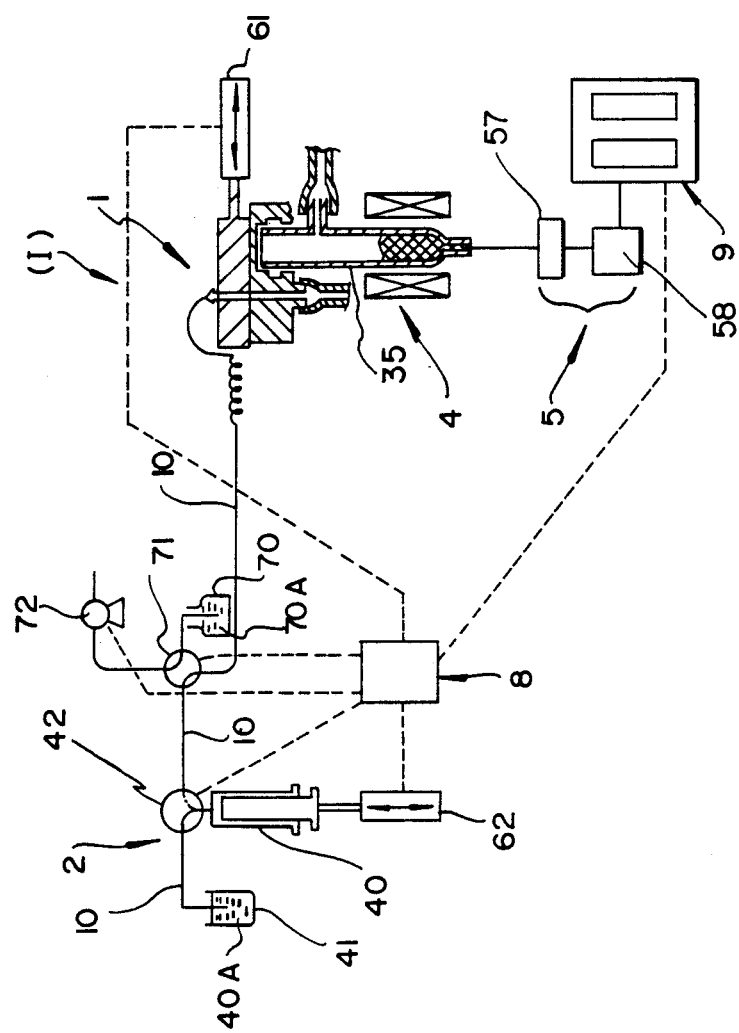
FIG. 3A shows combination of an injection unit, elevationally sectioned, in connection with a calibration unit and related devices, schematically drawn, of the present invention.

FIGS. 3A and 3B show an embodiment including the third featuring unit, wherein the carbon analyzer (I) has two flow routes: one is a usual or conventional sample route which extends from a sample container 41, on route, a micro-syringe unit 2, an injection unit 1, further to a combustion unit 4, an analytical unit 5; another new one, reference route, comprises a container of reference water 70, a pump 72 and a distinctive two-way switch valve 71, which is placed to intervene or to be tied in both the sample route and the reference route, with function that an equi-volume of both a sample water 40A and a reference water 70A will be exchanged momentarily by switching action. And as shown, the system additionally comprises in the whole a control unit 8 which will monitor and control, via drive means 61, 62, operations for measurement, pumping and injection of the two kinds of waters 40A, 70A for the preparative route and also comprised herein is a calibration control unit 9 which will compute and process data output from analytical devices 4, 5 concerning respective carbon analyses.

The micro-syringe unit 3 comprises a three way valve 42 tied in the sample flow route 10, a micro-syringe 40 associated to the valve 42, a control unit 8 which will act a piston to fill and to empty the syringe 40 as shown by a two opposite arrow mark in the box 62.

The injection unit 1 comprises, similar to other embodiments described before, a slide type injection device which is tightly connected or fitted to a combustion unit 4, specifically, to a combustion chamber 35, wherein it is to be noted that the injection unit 1 drawn in FIG. 3A is somewhat different from the inventive one described hereinbefore, for the reason of simplifying the drawings. And analytical measurement devices associated to the analytical control comprise a dehumidi-dustifier or clarifier 57 for gas from the combustion chamber 35, and a carbon dioxide analyzer 58, both being connected in series from the combustion chamber 35.

Turning to reference to the switch valve 71 (see FIG. 3B), shown is a four (4)-port two-way valve including a rotor 72 at center which comprises two separated flow ways 71A, 71B having an equal intra-volume respectively, which is assumed v $\mu$l (small v micro liter), and also comprised herein is a stator 73 which surrounds the round rotor 72 to form air-tight seal to prevent leakout from the flow routes, wherein the rotor 72 is supported to make diametric turns about a certain diameter so that connections of the two flow routes 71A, 71B will be exchanged so quickly and wherein the rotor 72 and the stator 73 are recommended to be made from polyfluoro resin in order to withstand possible chemicals present in the waters.

Operations in connection with those units and devices arranged to achieve calibrations are described below:

First, the carriage block in the injection unit 1 is set by action of the driver 61 so that injection hole bored through the carriage block is registered to the drain opening leading to discard wastes, and the three way valve 42 is set so that a passage noted in solid (not broken) line in the drawing FIG. 3A is communicated to the sample container 41. Then, the driver 62 moves the syringe 40 to suck or extract the sample water 40A into the syringe 40 and thereafter the passage in the three way valve 42 is switched so that passage or route from the syringe 40 to the injection 1 is open, whereinto the extracted water 40A is flown. These operations as noted are repeated sequentially to wash and to fill all spaces from the sample container 41 to the end of the injection unit 1, with the outstanding sample water 40A. Then, the carriage block is moved or switched to register with the top of the combustion chamber and, by action of the micro-syringe unit, the sample water 40A (V $\mu$l, large V micro liter) is injected to the chamber. The sample is subject to complete combustion, whereby carbon dioxide ($CO_2$) produced based on carbon-containing matters is sensed and measured by the carbon dioxide detector 58 and data $A_0$ (result of the first try with use of all sample water) is sent to be stored in the data processing unit 9.

In the next try or in the first calibration try, the reference route 70 is filled with a reference water 70A by action of the pump 72. In the meantime, the sample route 40 is filled with the sample water 40A as it was at the first try. Then, the four port valve 71 is actuated to turn the rotor 72 and the volume of v micro liter of the reference water 70A is replaced with the sample water 40A and then the partially replaced water is sent to injection as usual and output data $B_0$ is obtained at the following computerized unit 9.

Now workings move to the data processing unit 9, wherein, based on the data $A_0$ and $B_0$, a calibration coefficient S is calculated as follows:

$$S = v/V \times b \times 1/(B_0 - A_0)$$

wherein b is a reference water's carbon content which is previously input in the data processing unit.

Next, the sample water's carbon content $C_0$ is calculated as follows:

$$C_0 = A_0 \times S$$

Subsequently, V ml of another sample (not replaced with the reference water) is injected and measured of the detector output $A_1$, for which the analytical result $C_1$ is derived as follows:

$$C_1 = A_1 \times S$$

I claim:
1. An apparatus for feeding water to a water analyzer, comprising:
   an injection unit including,
   (a) a channel block having an elongated channel section with an elongated slide space therein, said channel section having an opening on a bottom of said slide space, wherein said channel block has a cylinder extending downward from said channel section and in air-tight communication with said opening, and further wherein said cylinder is connected with a cylindrical combustion chamber which is connected with a water analyzer,
   (b) a carriage block reciprocable within said slide space of said channel block, including a recessed area formed on a bottom of said carriage block facing said bottom of said slide space, such that at a first reciprocated position, said recess is in airtight communication with said opening and at a second reciprocated position, said recess is not in communication with said opening;
   an injection pipe having an injection end and a water receiving end, said injection pipe being fixed to said carriage block such that said injection end extends into said recessed area, but does not extend beyond the bottom of said carriage block, and is in air-tight communication with said opening at said first position; and a drive means for reciprocating said carriage block between said first and second positions.

2. The apparatus of claim 1, further comprising a microsyringe means for supplying water to be analyzed to the water receiving end of said injection pipe, said microsyringe means including a first and a second microsyringe, each being connected to a separate water supply by way of a first and second three-way valve, respectively, wherein said first three-way valve is connected between said first microsyringe, said water receiving end of said injection pipe, and said corresponding water supply, and said second three-way valve is connected between said second microsyringe, said corresponding water supply, and a point between said first three-way valve and the water supply of said first microsyringe, such that when water from the water supply of said first microsyringe is drawn into said first microsyringe, a predetermined amount of water previously stored in said second microsyringe is pumped out therefrom to merge with the water being drawn into said first microsyringe.

3. The apparatus of claim 1, further comprising a calibration means for intervening in a water supply route from a microsyringe unit to said water receiving end of said injection pipe, said calibration means including a reference water container, a pump, and a four-port two-way switch valve disposed therebetween, said switch valve also interposed between said microsyringe and said injection end wherein said four-port two-way switch valve has two separated passages, one for reference water from said reference water container and one for sample water from said microsyringe, such that upon switching said four-port two-way switch valve, the supply of sample water is exchanged with a supply of reference water to said water receiving end of said injection pipe to provide an intentional change in concentration of the sample water for calibration purposes.

* * * * *